United States Patent [19]

Wisniewski et al.

[11] Patent Number: 5,093,133
[45] Date of Patent: Mar. 3, 1992

[54] METHOD FOR PERCUTANEOUS DELIVERY OF IBUPROFEN USING HYDROALCOHOLIC GEL

[75] Inventors: Stephen J. Wisniewski, Doylestown; Mark Gemborys, Hatfield, both of Pa.

[73] Assignee: McNeil-PPC, Inc., Milltown, N.J.

[21] Appl. No.: 469,649

[22] Filed: Jan. 24, 1990

[51] Int. Cl.$^5$ .............................................. A61K 9/14
[52] U.S. Cl. .................. 424/484; 424/444; 424/488; 514/944
[58] Field of Search ............. 424/444, 484, 488; 514/944

[56] References Cited

U.S. PATENT DOCUMENTS

| 4,185,100 | 1/1980 | Rovee | 424/240 |
| 4,533,546 | 8/1985 | Kishi | 424/81 |
| 4,849,418 | 7/1989 | Lohner et al. | 514/163 |
| 4,877,620 | 10/1989 | Loew et al. | 424/451 |

FOREIGN PATENT DOCUMENTS 0151953 1/1985 United Kingdom .

OTHER PUBLICATIONS

S. S. Adams, Ph.D., P. Bresloff, Ph.D. and C. G. Mason, Ph.D., "The Optical Isomers of Ibuprofen", *Current Medical Research and Opinion*, vol. 3, No. 8, p. 552, (1975).

S. S. Adams, P. Bresloff, C. G. Mason, "Pharmacological Differences Between the Optical Isomers of Ibuprofen: Evidence for Metabolic Inversion of the (−)-Isomer", *J. Pharm. Pharmac.*, vol. 28, p. 256, (1976).

E. J. D. Lee, K. Williams, R. Day, G. Graham and D. Champion, "Stereoselective Disposition of Ibuprofen Enantiomers in Man", *Br. J. Clin., Pharmac.*, vol. 19, pp. 669-679, (1985).

K. M. Williams and R. O. Day, "Stereoselective Disposition—Basis for Variability in Response to NSAID's", *Birkhauser Verlag, Basel*, pp. 119-126, (1985).

*Primary Examiner*—Thurman K. Page
*Assistant Examiner*—Louis A. Piccone
*Attorney, Agent, or Firm*—Joseph J. Brindisi

[57] ABSTRACT

An ibuprofen containing hydroalcoholic gel of pH 3.5 to 6.0 for topically treating inflammation or pain comprising an effective amount of ibuprofen; 40 to 60% alcohol, e.g. ethanol or isopropyl alcohol; 0-20% of a non-volatile solvent, e.g. propylene glycol; 2.0 to 5.0% gelling agents, e.g. 2.5% hydroxypropyl cellulose or 4.0% polyacrylic acid polymer; sufficient base, e.g. triethanolamine, to adjust the pH to between 3.5 and 6.0; and water; methods for delivering ibuprofen through the skin to treat inflammation or pain using the hydroalcoholic gel; and use of substantially pure S-ibuprofen to topically treat such inflammation or pain.

5 Claims, 3 Drawing Sheets

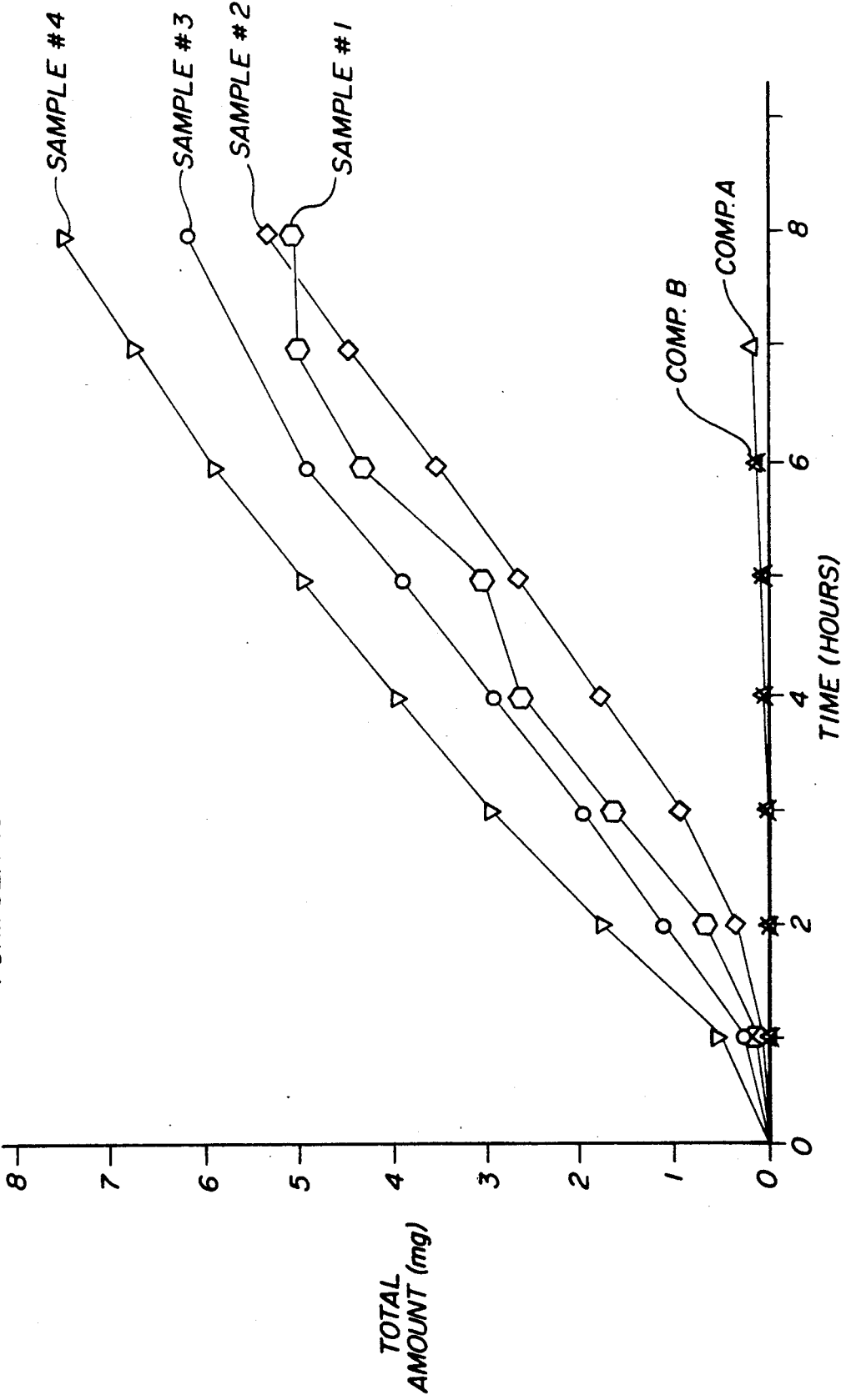

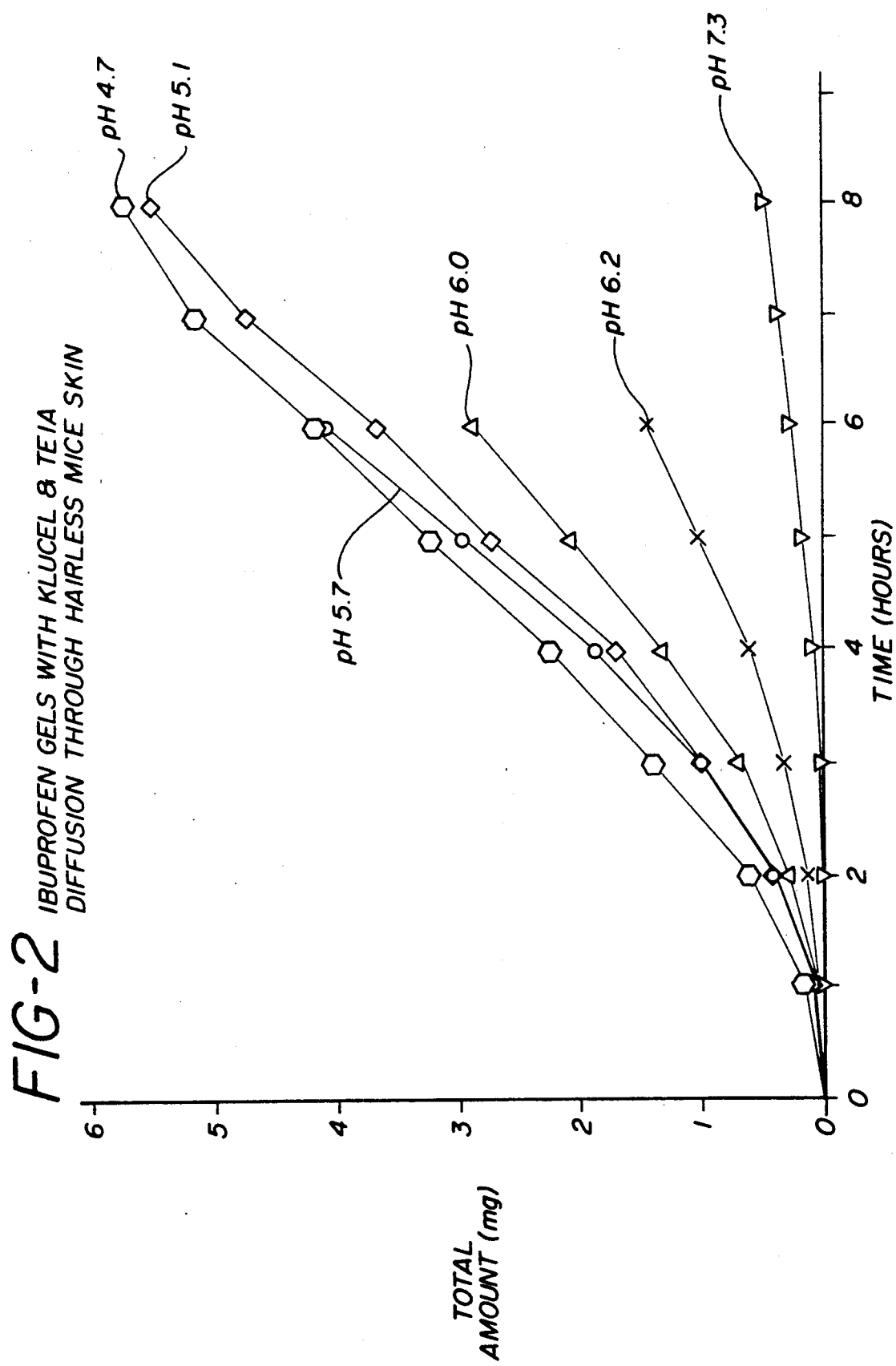

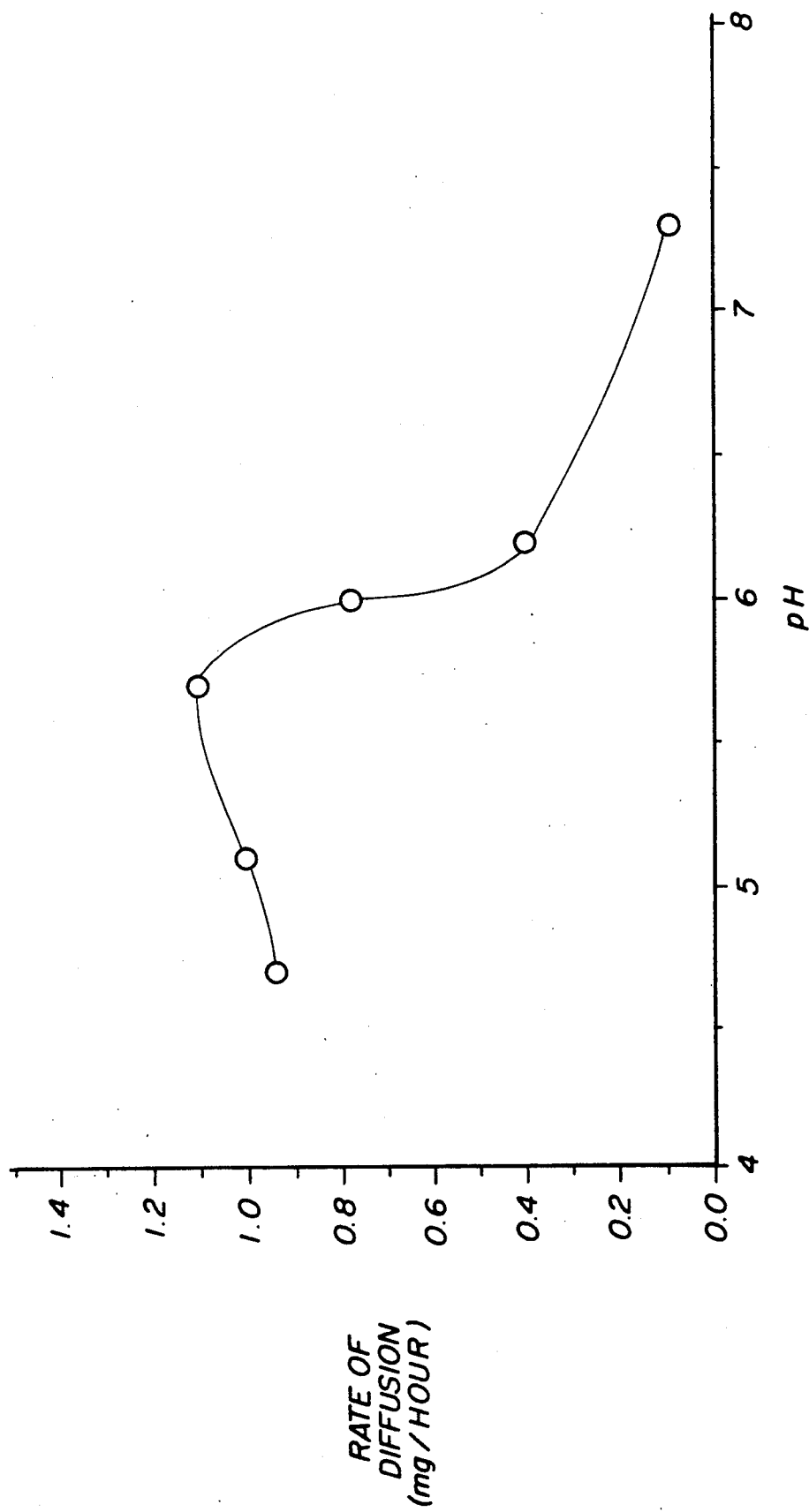

METHOD FOR PERCUTANEOUS DELIVERY OF IBUPROFEN USING HYDROALCOHOLIC GEL

This invention relates to a method for the topical delivery of the drug ibuprofen through the skin in order to treat conditions in the joints or soft tissue beneath the skin (e.g., inflammation and/or pain). More particularly, the invention relates to a percutaneous delivery system wherein the ibuprofen, preferably as the substantially pure S-enantiomer is incorporated into a hydroalcoholic gel of pH 3.5 to 6.0 and to such ibuprofen gel composition.

BACKGROUND INFORMATION

Ibuprofen is a well-known non-steroidal, anti-inflammatory (NSAID) drug having analgesic properties. It is mostly administered orally but can be administered topically as well. Ibuprofen has been marketed in the form of a cream in various foreign countries, e.g., as "Dolgit" in Germany and "Brufen" in Portugal. These ibuprofen creams are to be applied topically so that the ibuprofen is delivered in a percutaneous manner through the skin for its effect beneath the skin. The ibuprofen cream is, however, a poor delivery system, and the amount of ibuprofen actually penetrating the skin is very small.

U.S. Pat. No. 4,185,100 entitled "Topical Anti-Inflammatory Drug Therapy" describes a method of topical treatment of an inflammatory condition of the skin comprising applying to the affected area a non-steroidal anti-inflammatory agent and concurrently a topically active anti-inflammatory cortico-steroid, which are applied in a Pharmaceutically-acceptable topical vehicle selected from the group consisting of creams, gels, ointments, powders, aerosols and solutions suitable for topical administration. This patent does not indicate that one vehicle is more effective than any other vehicle.

Kyuki et al., "Anti-Inflammatory Effect of Diclofenac-Sodium Ointment (Cream) in Topical Application", *Japan J. Pharmacol.* 33, 121–132 (1983) describes the anti-inflammatory effect of a diclofenac-sodium. Ointments were prepared with three kinds of bases: lipophilic, emulsion (cream) and gel bases and their anti-inflammatory effects were compared. The cream base was reported by Kyaki et al. to have the most potent effect.

European Patent Application 0151953 to Beecham Group filed Jan. 17, 1985, published June 21, 1985 entitled "Topical Drug Release System" describes at page 10–11 an ibuprofen CARBOPOL gel system containing ibuprofen, propylene glycol, water, CARBOPOL 940 (polyacrylic acid polymer) and diisopropanolamine, as an illustrative example of a pharmaceutical composition for percutaneous absorption by topical application made in two liquid drug-containing phases, which are to be mixed together in situ just before use to form a supersaturated drug-containing gel. The EPO application discloses a non-alcoholic gel system for delivering ibuprofen topically. It has been unexpectedly found that the hydroalcoholic ibuprofen gels of the present invention at pH of 3.5 to 6.0 are more effective for delivering ibuprofen through the skin of a mammal than either the non-alcoholic ibuprofen gels as disclosed in Beecham's European patent application or the higher pH gels of Kishi et al.

U.S. Pat. No. 4,533,546 entitled "Anti-Inflammatory Analgesic Gelled Ointments" to Kishi et al. discloses NSAID, e.g. ibuprofen, containing hydroalcoholic gels having a pH in the range of 7.0 to 9.0. The gel ointment comprises a phenylacetic acid anti-inflammatory compound, a carboxyvinyl polymer, a water-soluble organic amine, e.g. triethanolamine and water wherein the amount of organic amine is such that the gel ointment has a pH in the range of 7.0 to 9.0 and preferably 7.3 to 7.8.

Ibuprofen (+)2-(p-isobutylphenyl)propionic acid is a racemic mixture of "S" and "R" enantiomer. It has been recognized in the art that the "S" form is the active component of ibuprofen in vitro but that in vivo the racemic mixture is believed to be of substantially equivalent potency because of the metabolic conversion of "R" to "S" by the body. See e.g. Adams et al., *Current Medical Research and Opinion*, "The Optical Isomers of Ibuprofen", Vol. 3, No. 8 Pg. 552 (1975) and *J. Pharm. Pharmac.*, "Pharmacological Differences Between the Optical Isomer of Ibuprofen: Evidence for Metabolic Conversion of the (−) Isomer", Vol. 28, Pg. 256 (1976); Lee et al., *Br. J. Clin. Pharmac.*, "Stereoselective Disposition of Ibuprofen Enantiomers in Man" Vol. 19, Pg. 669–674 (1985); and Williams et al., 1985 Birkhauser Verlay, Basel "Stereoselective Disposition Basis for Variability in Response to NSAID's" Pp. 119–126. The present inventors find, however, that the topical application of the substantially pure S-enantiomer of ibuprofen applied topically will provide greater analgesic and anti-inflammatory activity to the therapeutic site by not depending on metabolic conversion of the inactive R-enantiomer.

SUMMARY OF THE INVENTION

It is therefore an object of the present invention to provide a hydroalcoholic gel of pH 3.5 to 6.0 which is a significantly more effective vehicle than a cream, non-alcoholic or hydroalcoholic gel of pH above 7.0 for purposes of percutaneous delivery of ibuprofen through the skin.

As embodied and fully described herein the present invention provides a hydroalcoholic ibuprofen gel composition with a pH in the range of 3.5 to 6.0. In preferred embodiments of the invention, the ibuprofen hydroalcoholic gel comprises by weight of the total weight of the gel product from 5 to 15% ibuprofen; 0 to 20% of a non-volatile solvent, preferably propylene glycol; 40 to 60% alcohol; 2.0 to 5.0% gelling agents; sufficient base to adjust the pH to between 3.5 and 6.0; and water. In more preferred embodiments of the invention the ibuprofen is present in the range of 5 to 10%; the alcohol used is either ethanol or isopropyl alcohol; the gelling agent used is either hydroxypropyl cellulose or polyacrylic acid polymer; the base used is triethanolamine in a range of about 0.25 to 2%; and the pH is in the range of about 4.7 to 5.7. In referred embodiments the compositions of the invention consist essentially of the above-described components.

In further embodiments of the invention, the invention comprises a method for delivering ibuprofen through the skin in order to treat conditions situated beneath the skin which comprises incorporating ibuprofen into a carrier vehicle with a pH in the range of 3.5 to 6.0 and topically administering the ibuprofen to the skin of a patient. In more preferred embodiments the method comprises incorporating ibuprofen into a hydroalcoholic gel; adjusting the pH of the gel to between 3.5 and 6.0; and topically administering the ibuprofen containing gel to the skin of a patient.

In other embodiments of the invention, the ibuprofen, utilized in the composition and methods of the invention is the substantially pure S-enantiomer of ibuprofen (herein "S-ibuprofen"). The invention also includes a method for providing increased analgesic, anti-inflammatory, or analgesic and anti-inflammatory efficacy and speed of ac ion of ibuprofen comprising the step of topically administering substantially pure S-ibuprofen to the skin of a patient.

BRIEF DESCRIPTION OF THE DRAWINGS

FIG. 1 is a graph plotting the total amount of ibuprofen diffused through hairless mouse skin over time for different sample formulations of the gel of the invention and comparative examples. FIG. 2 is a graph plotting ibuprofen diffusion over time of sample gel formulations in accordance with the invention at various pHs. FIG. 3 is a graph plotting effect of pH on diffusion of ibuprofen through hairless mouse skin.

DETAILED DESCRIPTION OF THE INVENTION

The ibuprofen hydroalcoholic gels used in the process of the present invention are clear, spreadable, semisolid, jelly-like gels. These gels are made from alcohol and water utilizing a gelling agent such as, for example, hydroxypropylcellulose (HPC) (available from Hercules, Inc. as KLUCEL HF), or polyacrylic acid polymer (PAA) (available from B. F. Goodrich Chemical Col as CARBOPOL or CARBOMER 934P), with propylene glycol being an optional but preferred ingredient. An effective amount of ibuprofen and preferably substantially pure S-ibuprofen is incorporated into the gel.

Ibuprofen useful in accordance with this invention includes the conventionally used racemic mixture which comprises the S- and R-enantiomers of ibuprofen and preferably substantially pure S-ibuprofen. Substantially pure S-ibuprofen for the purposes of this specification means at least 90% by weight S-ibuprofen and 10% or less by weight of the R- enantiomer of ibuprofen. The S-enantiomer is known to be the active (i.e. analgesic and anti-inflammatory activity in mammals) component of conventional racemic ibuprofen but activity in vivo of the racemic mixture and substantially pure S-ibuprofen has been considered to be substantially equivalent, see for example, Adams et al., Curr. Med. Res. Opin., 3, 552 (1975) and *J. Pharm. Pharmacol., b 28, 256-257* (1976). This substantial equivalence of in vivo potency for the racemic mixture and S- forms is believed by Adams et al. to be due to the metabolic conversion of R- to S- in mammals. The present inventors find, as distinguished from Adams et al., that the S-ibuprofen form is more potent and faster acting in terms of analgesic and anti-inflammatory activity for topical applications.

The preferred hydroalcoholic gel formulations for use in the process of the present invention are as follows:

| Ingredient | % by wt |
| --- | --- |
| Ibuprofen | 5–15% |
| Propylene glycol | 0–20% |
| Alcohol USP (Ethanol-95%) | 40–60% |
| Gelling Agent: | |
| Hydroxypropyl Cellulose | about 2.5% |

-continued

| Ingredient | % by wt |
| --- | --- |
| (HPC) (KLUCEL HF) [or polyacrylic acid polymer] (PAA) (CARBOPOL 934P) | about 4.0% |
| H₂O | q.s. to 100 |
| Base (e.g. Trolamine N.F.) | a sufficient amount to adjust pH 3.5–6 |

In the ibuprofen-hydroalcoholic gel formulations useful in the present invention, it is possible to use lesser or greater amounts of ibuprofen than shown above if desired, e.g., as little as 1 percent can be used particularly if the more active substantially pure S-ibuprofen is used, or as much as 20 percent or more can be used if desired. Best results in terms of the delivery rate of ibuprofen through the skin are obtained using a preferred amount of 5–15 percent by weight of ibuprofen or substantially pure S-ibuprofen.

Preferably, a non-volatile solvent, e.g. propylene glycol, is used in the gels of the present invention as an optional ingredient to improve the spreading properties and aesthetics of the gel to, e.g. minimize any congealing or balling up or drying of the gel when it is rubbed on the skin. This ingredient is not critical in the sense that it does not appear to alter the delivery rate of ibuprofen through the skin. For the above reasons it is a preferred ingredient in amounts of about five percent (5%). Propylene glycol also acts as a humectant in the hydroalcoholic gels of the invention. Substitutes for propylene glycol may include, for example, propylene glycol esters and glycerine.

In the hydroalcoholic gels of the present invention, it may be possible to vary the amounts of ethanol used beyond those preferred amounts (40–60%) specified above. Preferably the amount used will produce a saturated or almost saturated solution of ibuprofen in the final gel preparation. The minimum amount of alcohol applied is that amount to dissolve the only very slightly water soluble ibuprofen (particularly at acidic pHs). Thus, one would normally use more alcohol with a greater amount of ibuprofen than with a lesser amount of ibuprofen. Commercially, denatured alcohol such as SDA-40 is often used in place of Alcohol USP (ethanol), and it may be used here also. While ethanol is the preferred alcohol, isopropyl alcohol and other pharmaceutically acceptable alcohols may be used in this invention.

It has also been found that good results are obtained by substituting PAA, e.g., CARBOPOL 934P for HPC, e.g., KLUCEL HF, as the gelling agent. Other gelling agents may be alternatively used in this invention provided they are compatible with the hydroalcoholic system, i.e., are capable of forming a gel with the amount of alcohol and water required to solubilize ibuprofen. Many well known gelling agents may not, however, form gels under these conditions in this system.

The requisite amount of gelling agent used in this invention is an amount needed to obtain a desirable gel. If too much gelling agent is used the resultant gel will be too stiff. One should therefore use as little gelling agent as is necessary to get the physical form of gel desired generally in the range of about 2.0 to 5.0%. Preferably, this amount is about 2.5% with HPC, or 4.0% with PAA as the gelling agent. The resultant desirable gels are clear, spreadable, and semi-solid jelly-like gels Preferably, the hydroalcoholic gels for use in the process of the Present invention will have a viscosity of within the range above 150,000 to about 400,000 centipoise (cps), but use of an even broader range of viscosities is possible. The gel formulation should behave as a solid at zero shear and yet be easily spread under low shear conditions, such as by rubbing of the gel formulation on the skin.

The rate of delivery of ibuprofen percutaneously has been surprisingly found to be acid pH dependent, so the pH of the gels may need to be adjusted to desirable levels. The optimum rates of percutaneous delivery are from hydroalcoholic gels with a pH of 3.5 to 6.0 and preferably 4.7 to 5.7. The previously discussed patent to Kishi et al. in fact contrarily teaches that hydroalcoholic gels for delivery of NSAIDs including ibuprofen should have a pH of from 7.0 to 9.0.

Most gelling agents usable in accordance with the present invention, are generally very acidic and thus bring the pH below the desirable range of 3.5 to 6.0. The pH is preferably adjusted by the addition of triethanolamine (trolamine N.F.), or sodium hydroxide or any other compatible, pharmaceutically acceptable base or alkalizing agent. The ibuprofen-hydroalcoholic gels of the present invention are useful in a pH range of 3.5 to 6.0, with a pH of 4.7 to 5.7 being the preferred range for obtaining the optimum delivery rate as is demonstrated in the Examples section below.

Preservatives such as methylparaben and propylparaben and other phamaceutically acceptable preservatives may be added to the gels to enhance microbial activity.

Emollients, humectants, counterirritants and other pharmaceutical excipients as well as fragrances may be added to the basic formulations of the invention.

In testing the relative amount of ibuprofen able to penetrate the skin in a mouse test, it was found that the amount of ibuprofen delivered using the most preferred hydroalcoholic gel of the present invention at a pH in the range of 3.5 to 5.0, preferably in the range 4.7 to 5.7, is much greater than the amount delivered using a cream base. The gels of the present invention are thus many times more effective than a cream base for delivering ibuprofen percutaneously. The effectiveness of the invention is demonstrated in the following examples section.

The invention will now be illustrated by examples. The examples are not intended to be limiting of the scope of the present invention but read in conjunction with the detailed and general description above, provide further understanding of the present invention and an outline of a process for preparing the compositions of the invention.

EXAMPLES

EXAMPLE I IBUPROFEN TOPICAL GEL. 10% w/w

The following formulation was used in the Example and was made into a gel by the procedure which follows:

| A. Ingredients | g/100 g |
|---|---|
| S-ibuprofen (SEPRACOR, INC.) | 10.0 |
| (Substantially pure, about 97% S-ibuprofen w/w) | |
| Alcohol USP | 54.0 |
| Propylene Glycol USP (PG) | 5.0 |
| Purified Water USP | 28.25 |
| Methylparaben NF | 0.1 |

| A. Ingredients | g/100 g |
|---|---|
| Propylparaben NF | 0.1 |
| Triethanolamine (TROLAMINE NF) | 0.25 |
| Hydroxypropyl Cellulose NF (HPC) (KLUCEL HF) | 2.5 |
| (Apparent viscosity 1500–2500 cps) | |

B. Manufacturing Directions

1. Dissolve the ibuprofen or substantially pure S-ibuprofen in the alcohol in a suitable stainless steel container with mild agitation.
2. Dissolve the propylene glycol, methylparaben and propylparaben in the alcohol/ibuprofen solution.
3. Add the water and trolamine and continue mixing.
4. Add the hydroxypropyl cellulose to the solution and continue to mix until a clear gel is formed (approximately four hours).
5. Seal the container and allow air bubbles to diffuse out of the gel.
6. Fill into 30 g. aluminum tubes and seal.
7. Obtain an ibuprofen hydroalcoholic gel of apparent pH about 5.1.

EXAMPLES II to VIII

Following the procedure described in Example I, but using the following formulations shown as the ingredients thereof, in each case a hydroalcoholic gel was obtained, having a PH indicated.

EXAMPLE II

Utilizing the same formulation as Example I, except conventional racemio ibuprofen was used in place of substantially pure S-ibuprofen.

EXAMPLE III

| Ibuprofen (racemic) | 5.0 | pH:4.7 |
|---|---|---|
| Alcohol USP | 43.9 | |
| Methyl Paraben | 0.1 | |
| Propyl Paraben | 0.1 | |
| Propylene Glycol | 10.0 | |
| KLUCEL HF | 2.5 | |
| Triethanolamine | 0.1 | |
| Water | 38.3 | |

EXAMPLE IV

| Ibuprofen (racemic) | 5.0 | pH:5.1 |
|---|---|---|
| Alcohol USP | 44.2 | |
| Water | 37.9 | |
| Methyl Paraben | 0.1 | |
| Propyl Paraben | 0.1 | |
| Propylene Glycol | 10.0 | |
| KLUCEL HF | 2.5 | |
| Triethanolamine | 0.25 | |

EXAMPLE V

| Ibuprofen (racemic) | 5.0 | pH:5.7 |
|---|---|---|
| Alcohol USP | 43.9 | |
| Methol Paraben | 0.1 | |
| Propyl Paraben | 0.1 | |
| Water | 37.9 | |
| Propylene Glycol | 10.0 | |
| KLUCEL HF | 2.5 | |

-continued

| | |
|---|---|
| Triethanolamine | 0.5 |

EXAMPLE VI

| | | |
|---|---|---|
| Ibuprofen (racemic) | 5.0 | pH:6.0 |
| Alcohol USP | 43.4 | |
| Methyl Paraben | 0.1 | |
| Propyl Paraben | 0.1 | |
| Water | 37.9 | |
| Propylene Glycol | 10.0 | |
| KLUCEL HF | 2.5 | |
| Triethanolamine | 1.0 | |

COMPARATIVE EXAMPLE VII

| | | |
|---|---|---|
| Ibuprofen (racemic) | 5.0 | pH:6.2 |
| Alcohol USP | 42.9 | |
| Methol Paraben | 0.1 | |
| Propyl Paraben | 0.1 | |
| Water | 36.9 | |
| Propylene Glycol | 10.0 | |
| KLUCEL HF | 2.5 | |
| Triethanolamine | 2.0 | |

COMPARATIVE EXAMPLE VIII

| | | |
|---|---|---|
| Alcohol USP | 45.9 | pH:7.3 |
| Ibuprofen (racemic) | 5.0 | |
| Methyl Paraben | 0.1 | |
| Propyl Paraben | 0.1 | |
| Water | 42.4 | |
| KLUCEL HF | 2.5 | |
| Triethanolamine | 4.0 | |

Test Procedure Used

The various hydroalcoholic ibuprofen formulations referred to herein are tested for their relative effect in delivering ibuprofen through skin, by a mouse test procedure, as follows:

Skin, freshly excised from the abdominal region of 8-12 week old hairless mice is refrigerated at 15° C. overnight. The skin is removed and placed in a modified Franz (Crown Glass) cell with the dermal side in contact with a phosphate buffer at pH 7.4±0.1 thermostatted at 37° C.±o.5°. The formulation is placed on the stratum corneum. Samples of phosphate buffer are assayed for ibuprofen at regular intervals using high pressure liquid chromatography. A plot of total amount of ibuprofen transported through the skin vs. time is prepared to identify the formulation with the minimum rate of percutaneous delivery.

Test Results

Various gels of this invention (whose formulations are shown above in the Examples) and of the prior art are tested, according to the above mouse test procedure. The tests measured the total amount of ibuprofen (in milligrams) which diffuses through mouse skin at various time intervals, and the results are plotted on the graphs of FIG. 1 and FIG. 2 in the accompanying drawings.

FIG. 1 is a graph comparing the total amount of ibuprofen diffused through mouse skin over various time intervals between zero hours and 8 hours for each of the following 6 different sample formulations whereby samples 1–4 corresponding to Examples IX-XII are prepared in accordance with the invention and the procedure of Example I:

| Test Sample # | Ingredients | % by wt. | Corresponding Example No. |
|---|---|---|---|
| 1. | Ibuprofen (milled) | 5.0 | IX |
| | Alcohol USP | 50.0 | |
| | Methyl Paraben | 0.1 | |
| | Propyl Paraben | 0.1 | |
| | Water | 42.5 | |
| | Klucel HF | 2.5 | |
| 2. | Ibuprofen (milled) | 5.0 | X |
| | Alcohol USP | 47.0 | |
| | Methyl Paraben | 0.1 | |
| | Propyl Paraben | 0.1 | |
| | Water | 40.5 | |
| | Klucel HF | 2.5 | |
| | Propylene Glycol | 5.0 | |
| 3. | Ibuprofen (milled) | 10.0 | XI |
| | Alcohol USP | 47.0 | |
| | Methyl Paraben | 0.1 | |
| | Propyl Paraben | 0.1 | |
| | Water | 35.5 | |
| | Klucel HF | 2.5 | |
| | Urea | 5.0 | |
| 4. | Ibuprofen (milled) | 10.0 | XII |
| | Alcohol USP | 40.0 | |
| | Propylene Glycol | 5.0 | |
| | Water | 39.0 | |
| | Carbopol 934P | 4.0 | |
| | Triethanolamine | 2.0 | |

Comp. A BRUFEN Creme containing 10% ibuprofen, (Boots Ltd., Italy and Portugal)

Comp B DOLGIT Creme containing 5% ibuprofen, (Dolorgiet Phamaceuticals, Germany)

Note: Values listed are total amount diffused in units of milligrams.

As can be seen, comparative samples A and B, which represent the prior art ibuprofen creams, are much less effective than the gels of this invention.

FIG. 2 is a graph comparing 6 sample gel formulations, all containing 5% ibuprofen, but at a different pH, as follows:

| Corresponding Example No. | pH |
|---|---|
| III | 4.7 |
| IV | 5.1 |
| V | 5.7 |
| VI | 6.0 |
| Comp. VII | 6.2 |
| Comp. VIII | 7.3 |

As can be seen from FIG. 2, Sample 5 which is outside the preferred pH range of the invention and Sample 6 whose pH is outside of the scope of the present invention are much less effective than the gels which have a PH in the claimed range of the invention in terms of diffusion through the skin.

FIG. 3 is a graph of the rate of diffusion (mg/hour) of ibuprofen through hairless mouse skin at varying pHs as cited above for Examples III - comp. VIII (i.e. pH 4.7 to 7.3).

The scope of the present invention is not limited by the description, examples and suggested uses herein and modifications can be made without departing from the spirit of the invention. For example, additional medicaments or counter-irritants such as methyl salicylate or menthol may be added to the hydroalcoholic gel to provide a combination medication. Alcohol may be replaced with a pharmaceutically acceptable organic solvent that provides the equivalent function of solubilizing ibuprofen. Further, the pharmaceutical gels of the invention may be utilized for non-medicament ingredients including cosmetics or nutrients such as vitamins and minerals.

Application of the compositions and method of the present invention for medical and pharmaceutical uses can be accomplished by any clinical, medical and pharmaceutical methods and techniques as are presently or prospectively known to those skilled in the art. Thus it is intended that the present invention cover the modifications and variations of this invention provided that they come within the scope of the appended claims and their equivalents.

What is claimed is:

1. An ibuprofen hydroalcoholic gel composition consisting essentially of by weight of the total weight of the composition: about 1 to 15% substantially pure S-ibuprofen; 0 to 20% of propylene glycol; about 40 to 60% alcohol; about 2.0 to 5.0% of a gelling agent selected from the group consisting of hydroxy propyl cellulose and polyacylic acid polymens sufficient triethanolamine to adjust the pH to a range of from 3.5 to 6.0 which is about 0.25 to 2%; and water q.s. to 100%.

2. An ibuprofen hydroalcoholic gel composition consisting essentially of by weight of the total weight of the composition: about 1 to 15% of substantially pure S-ibuprofen; about 5% propylene glycol; about 40 to 60 % alcohol; about 2.5% of hydroxypropyl cellulose or about 4% of polyacrylic acid polymer; a sufficient amount of triethanolamine to adjust the pH to a range of from 4.7 to 5.7 which is about 0.25 to 2%; and water q.s. to 100%.

3. A method for delivering the drug ibuprofen through the skin in order to treat inflammation or pain beneath the skin which comprises the steps of: incorporating an anti-inflammatory or analgesic effective amount of substantially pure S-ibuprofen into a hydroalcoholic gel; adjusting the pH of the gel to between 3.5 and 6.0; and topically administering said ibuprofen-containing gel to the skin of a patient, wherein the ibuprofen-hydroalcoholic gel administered has the following formulation in percent by weight of the total weight of the gel: about 1 to 15% of substantially pure S-ibuprofen; about 0 to 20% of a non-volatile solvent; about 40 to 60% an alcohol selected from the group consisting of ethanol and isopropyl alcohol; about 2.0 to 5.0% a gelling agent selected from the group consisting of hydroxypropyl cellulose and polyacrylic acid polymer; sufficient triethanolamine to adjust pH to 3.5 to 6, which is about 0.25 to 2% and water q.s. to 100%.

4. A method for delivering the drug ibuprofen through the skin in order to treat inflammation or pain beneath the skin which comprises the steps of: incorporating an anti-inflammatory or analgesic effective amount of substantially pure S-ibuprofen into a hydroalcoholic gel; adjusting the pH of the gel to between 3.5 and 6.0; and topically administering said ibuprofen-containing gel to the skin of a patient, wherein the ibuprofen-hydroalcoholic gel administered has the following formulation in percent by weight of the total weight of the gel: about 1 to 15% of substantially pure S-ibuprofen; about 0 to 20% of a non-volatile solvent; about 40 to 60% of ethanol or isopropyl alcohol; about 2.0 to 5.0% of hydroxypropyl cellulose or polyacrylic acid polymer and sufficient triethanolamine to adjust pH to 3.5 to 6; and water q.s. to 100%.

5. An ibuprofen hydroalcoholic gel composition consisting essentially of by weight of the total weight of the composition: about 1 to 15% of substantially pure S-ibuprofen; about 5% propylene glycol; about 40 to 60% alcohol; about 2.5% of hydroxypropyl cellulose or about 4% of polyacrylic acid polymer; a sufficient amount of triethanolamine to adjust the pH to a range of from 4.7 to 5.7; and water q.s. to 100%.

* * * * *